United States Patent [19]
Ingram

[11] Patent Number: 5,086,761
[45] Date of Patent: Feb. 11, 1992

[54] MULTI-ADJUSTABLE KNEE BRACE

[76] Inventor: Patrick T. Ingram, 9800 Sheridan St. #205, Pembroke Pines, Fla. 33024

[21] Appl. No.: 498,909

[22] Filed: Mar. 26, 1990

[51] Int. Cl.⁵ ............................................. A61F 5/00
[52] U.S. Cl. ....................................................... 602/26
[58] Field of Search ............... 128/77, 80 R, 80 C, 128/157, 165, 155, 166; 2/22, 24

[56] References Cited

U.S. PATENT DOCUMENTS

| | | | |
|---|---|---|---|
| 1,428,465 | 5/1922 | Willmott | 128/165 |
| 1,622,211 | 3/1927 | Sheehan | 128/165 X |
| 3,046,981 | 7/1962 | Biggs, Jr. et al. | 128/80 C |
| 3,074,400 | 1/1963 | Schulman | 128/80 C |
| 3,084,685 | 4/1963 | Lewis | 128/80 C |
| 3,551,912 | 1/1971 | Viglione | 2/24 |
| 3,703,171 | 11/1972 | Schiavitto | 128/80 C |
| 3,786,804 | 1/1974 | Lewis | 128/80 C |
| 3,804,084 | 4/1974 | Lehman | 128/165 X |
| 3,934,583 | 1/1976 | Hollingshead et al. | 128/80 C X |
| 3,945,046 | 3/1976 | Stromgren | 128/80 C X |
| 4,064,874 | 12/1977 | Valin | 128/80 C |
| 4,084,584 | 4/1978 | Detty | 128/80 C |
| 4,084,586 | 4/1978 | Hettick | 128/80 C X |
| 4,116,236 | 9/1978 | Albert | 128/80 C |
| 4,250,578 | 2/1981 | Barlow | 128/80 C X |
| 4,287,885 | 9/1981 | Applegate | 128/80 C |
| 4,296,744 | 10/1981 | Palumbo | 128/80 C |
| 4,353,362 | 10/1982 | De Marco | 128/80 C |
| 4,366,813 | 1/1983 | Nelson | 128/80 C |
| 4,370,978 | 2/1983 | Palumbo | 128/80 C |
| 4,378,009 | 3/1983 | Rowley et al. | 128/83 |
| 4,423,720 | 1/1984 | Meier et al. | 128/80 C |
| 4,425,912 | 1/1984 | Harper | 2/24 X |
| 4,474,573 | 10/1984 | Detty | 128/80 C |
| 4,492,227 | 1/1985 | Senn et al. | 128/80 C |
| 4,494,247 | 1/1985 | Kelly | 2/24 |
| 4,651,722 | 3/1987 | Karczewski | 128/80 C |
| 4,693,241 | 9/1987 | Trznadel | 128/157 |
| 4,724,831 | 2/1988 | Huntjens | 128/165 X |
| 4,765,318 | 8/1988 | Tranberg et al. | 128/80 C |
| 4,791,916 | 12/1988 | Paez | 128/80 C |
| 4,805,606 | 2/1989 | McDavid, III | 128/80 C |
| 4,822,371 | 4/1989 | Jolly et al. | 128/80 C X |
| 4,832,010 | 5/1989 | Lerman | 128/80 C X |
| 4,854,308 | 8/1989 | Drillio | 128/80 C |
| 4,870,956 | 10/1989 | Fatool et al. | 128/80 C |
| 4,872,448 | 10/1989 | Johnson, Jr. | 128/80 C |
| 4,938,207 | 7/1990 | Vargo | 128/80 C |

FOREIGN PATENT DOCUMENTS

| | | | |
|---|---|---|---|
| 0329815 | 8/1989 | European Pat. Off. | 128/80 C |
| 0532262 | 8/1931 | Fed. Rep. of Germany | 128/165 |
| 2532839 | 3/1984 | France | 128/80 C |
| 2633512 | 1/1990 | France | 128/80 C |
| 2636228 | 3/1990 | France | 128/80 C |

Primary Examiner—Richard J. Apley
Assistant Examiner—Linda C. M. Dvorak

[57] ABSTRACT

A multi-adjustable knee brace or wrap for use during athletic or other activity to prevent the kneecap from slippage out of operable location and to reduce strain on damaged ligaments and/or muscle tissue. The knee brace includes a tubular, adjustable, stretchable sleeve configured to snugly embrace the knee and to attach to the knee without having to slide the knee brace over the foot and calf; a pair of stretchable straps anchored to the front of the sleeve and disposed for criss-cross wrapping across the front of the kneecap and around to the back of the knee; a pair of soft, non-rigid hooks anchored to the sleeve and disposed for hooking each of the elastic straps in criss-cross relation; and, VELCRO-type material above and below the knee of the sleeve and on the end portion's of each of the ealstic straps for adjustable anchoring of the ends of each of the elastic strips on the sleeve.

8 Claims, 3 Drawing Sheets

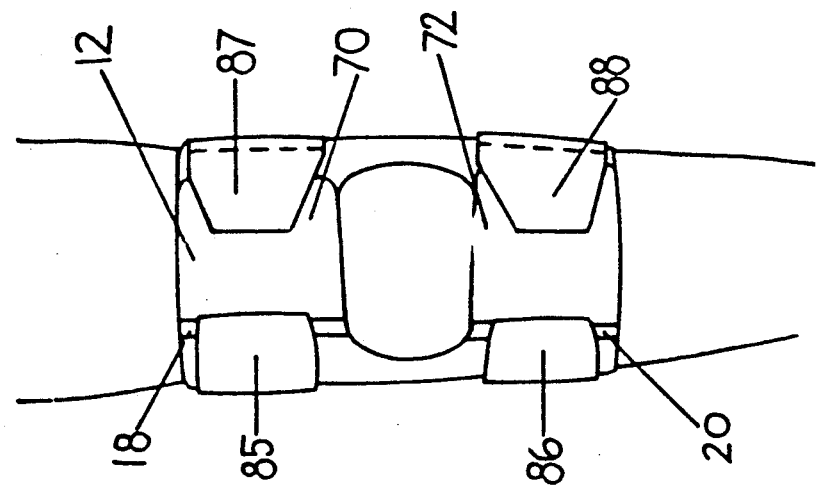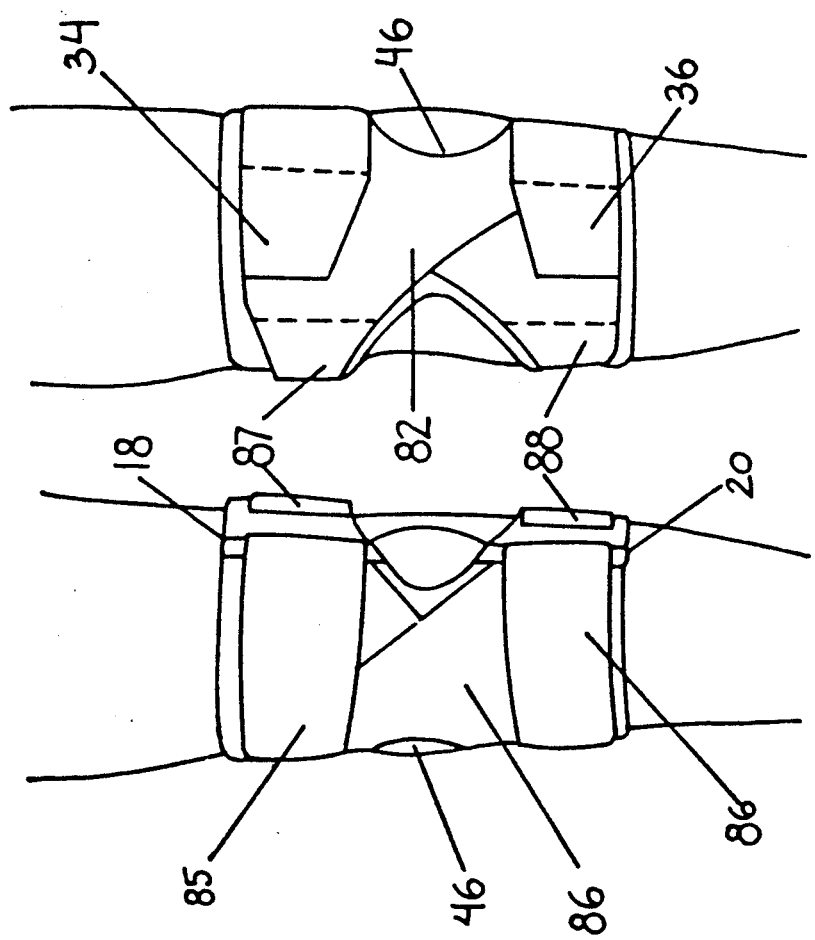

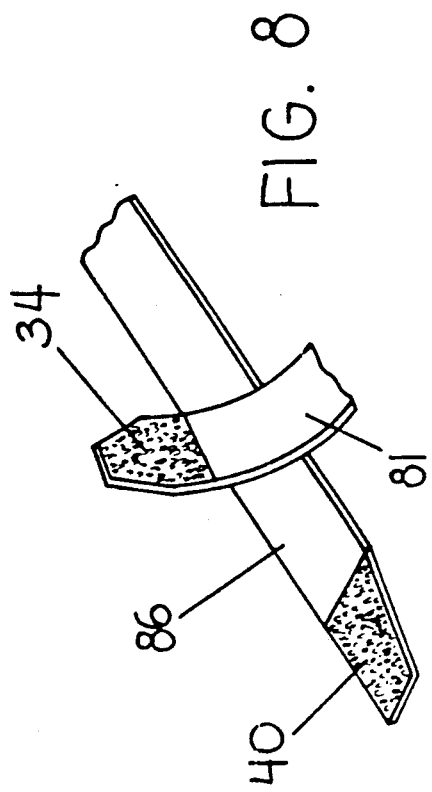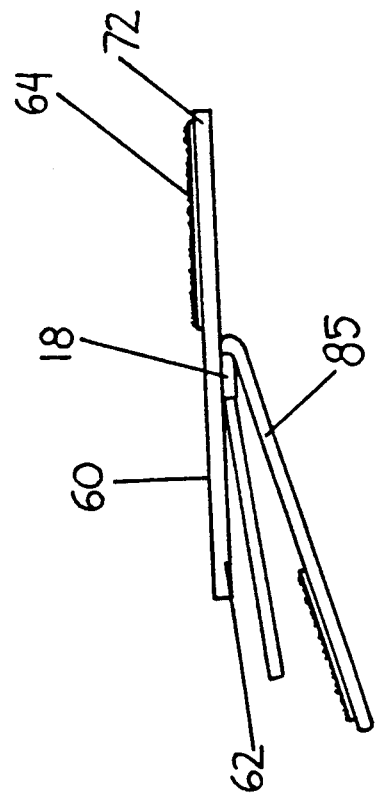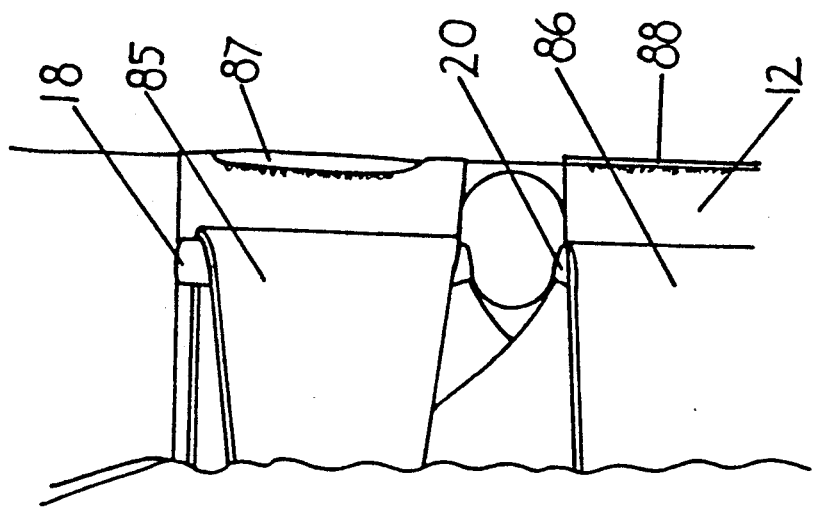

MULTI-ADJUSTABLE KNEE BRACE

BACKGROUND OF THE INVENTION

1. Field of the Invention

A knee brace or wrap of the type including a tubular, adjustable, elastic or stretchable sleeve with elastic or stretchable straps disposed to be adjustably criss-crossed over a kneecap and held in position across the kneecap by corresponding soft, non-rigid hooks and fasteners.

2. Description of the Prior Art

In the past various knee braces have been developed to assist persons with damaged muscle tissue, cartilage and ligaments in the knee area. Unfortunately, none of these braces have been perfectly successful functionally and/or aesthetically for athletes and persons in otherwise active lives. These persons have continued to be plagued by knees being thrown out or being further damaged or are forced to use bulky restrictive and/or inadequate supports.

In some cases, simple elastic sleeves have been developed to snugly hold the knee. The advantage of this design is simplicity in usage and appearance; but, the disadvantage is that the elastic either stretches out of shape or is too tight and restrictive to movement. In other cases, more complicated structures have been developed which have a multitude of deficiencies including restricting movement, loss of lateral support during bending of the knee, having metal or other structural components which may rub or injure a wearer particularly in the event of collision or fall, complexity in use, unattractiveness, non-functionality, etcetera.

SUMMARY OF THE INVENTION

The present invention is directed to multi-adjustable knee brace specifically designed to be used to provide support to a user's knee while permitting substantial freedom of movement. In operation, the knee brace is structured to be adjusted in tension across the kneecap in two opposing directions so as to cup the kneecap in a particular location relative to the sides of the leg, and, to the calf and thigh and without losing tension at the sides of the knee joint when the knee is in a bent position. The subject knee brace enables the versatile, protected motion of the knee without use of structural components and non-attractive contraptions.

More specifically, the subject knee brace comprises an elastic or stretchable sleeve configured to snugly embrace the knee; a pair of elastic or stretchable straps anchored to the front of the sleeve at above and below the kneecap opening and disposed for criss-cross wrapping across the front of the kneecap and around to the back of the knee; a pair of soft, non-rigid hooks anchored to the sleeve and disposed for hooking two of the elastic strap portions in criss-cross relation; and hook and loop fastening material (of the type commonly sold under the trademark VELCRO) material above and below the knee of the sleeve and on the end portions of each of the elastic straps for adjustable anchoring of the ends of each of the elastic straps on the sleeve. The elastic straps, soft, non-rigid hooks, and VELCRO fasteners of the subject knee brace according to the need of the user with minimum adjustments and inconvenience. The elastic straps, when criss-cross, hooked, and fastened, form part of the support fabric extending above and below the kneecap upon which the knee brace is positioned.

An object of the present invention is to provide a knee brace that is simple in usage and appearance.

Another object of the present invention is to provide a knee brace that is multi-adjustable.

Another object of the present invnetion is to provide a knee brace that is not overly restrictive to knee movement.

Another object of the present invention is to provide a knee brace that reduces the risk of injury to a user in the event of collision or fall.

Another object of the present invention is to provide a knee brace that includes a simple means for adjusting and maintaining tension over the kneecap with a pair of straps in criss-crossed relation, so as to support the kneecap from every conceivable angle in a surrounding design while also supporting the sides of the knee when in a bent position.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

The novel and distinctive features of the present invention are set forth in the claims appended hereto. For a fuller understanding of the nature of the present invention, reference should be had to the following detailed description taken in conjunction with the accompanying drawings in which:

FIG. 3 is a perspective view of the knee brace with elastic or stretchable straps hooked and fastened.

FIGS. 4, 5, & 6 are a left side, right side and rear view showing the knee brace in its operative position over a knee of a user.

FIG. 7 is a perspective downward view of a knee brace with elastic of stretchable strap reversing direction through soft, non-rigid hook.

FIG. 8 is a perspective view of elastic or stretchable strap ends with VELCRO-type material sewn in.

Like reference numerals refer to like parts throughout the several view of the drawings.

DETAILED DESCRIPTION OF THE PREFERRED EMBODIMENT

Figure 2:
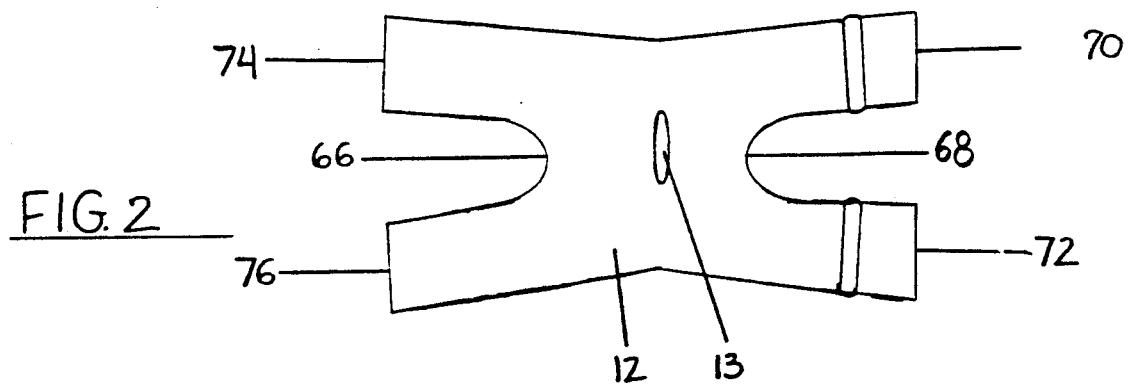
FIG. 2 is a perspective view of the knee brace without the tensioning straps attached.
Figure 1:
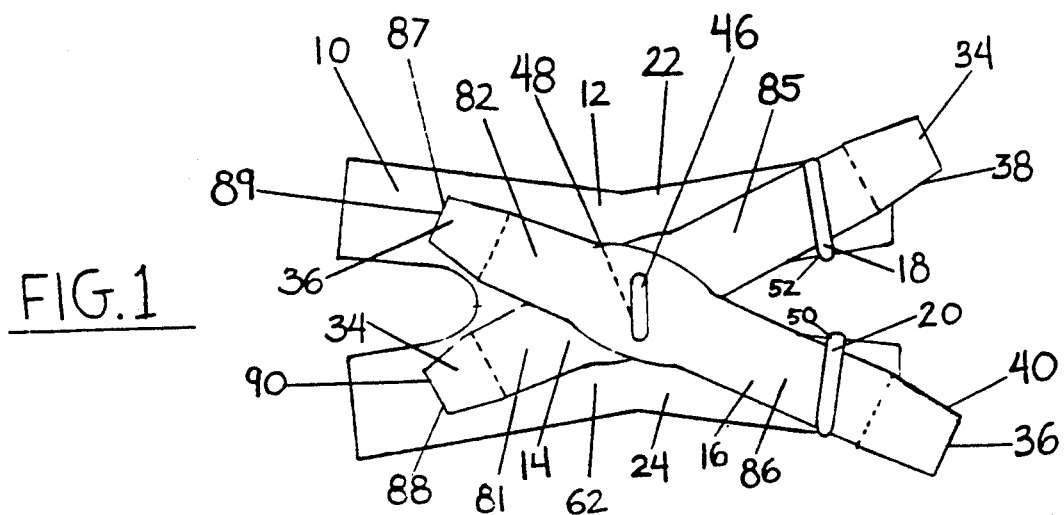
FIG. 1 is a perspective view of the knee brace of the present invention shown.

As shown in FIGS. 1 through 8, the present invention is directed towards a multi-adjustable knee brace or wrap, generally indicated as 10, for use during athletic or other activity to prevent the kneecap from slippage out of operable location and to reduce strain on damaged ligaments. The knee brace 10 is comprised of a sleeve 12, a pair of straps 14 and 16 and a pair of soft, non-rigid hooks 18 and 20.

The sleeve 12 is comprised of a specially cut pattern of composite stretchable material which is wrap-able about the knee joint and knee region of a user in order to create a snug fitting, tubular shaped having an entrance and exit through which the thigh and calf regions of a wearer may extend while in position about the knee. The sleeve 12 has an interior region 60 made of elastic or stretchable material, such as neoprene, configured to snugly embrace the skin about the kneecap and knee region, and, exterior region 62 bonded to the interior region 60 and made of stretchable VELCRO-loop material. VELCRO-hook material 64 is sewn or adhered to flaps 70 and 72 on the interior region 60 for mateable engagement with flaps 74 and 76, respectively, on the exterior region 62. Therefore, as the sleeve 12 is drawn about the knee region commencing from the back of the knee region with the flaps 74 and 76, pulled forward about the kneecap and around to the back of the knee region, the VELCRO-hook material of the flaps 70 and 72 engages the VELCRO-loop material of the flaps 74 and 76, respectively, to provide the desired snugness of the sleeve 12 about the kneecap and knee region of the user. When engaged as aforestated, insert cut portions 66 and 68 provide an open space behind the knee for non-restrictive movement. The opening 13 is positioned to lie directly over the kneecap to allow the kneecap to protrude as not to create any direct pressure downward on the kneecap and, at the same time, cupping all sides of the kneecap. This opening 13 is shaped as an elongated oval so that the kneecap will have constant protrusion when the knee is first bent and then the kneecap moves slightly downward. The sleeve 12 includes an upper portion 22 extending above the knee into the thigh region and a lower portion 24 extending below the knee into the calf region.

The straps 14 and 16 are made of elastic or stretchable composite material, such as a composite material having an outer layer of flexible nylon, a middle layer of closed cell neoprene and an inner layer of flexible nylon. The outer material being chosen to avoid catching or grabbing when a user falls or has contact with other surfaces that might twist or otherwise damage the knee. The straps 14 and 16 are separately anchored with stitching above and below apertures 46 and 48 on straps 14 and 16 to thigh and calf region directly above and below the kneecap opening 13 of sleeve 12. Straps 14 and 16 are situated to rest centered on the front of the knee overlapping in a criss-cross fashion. The exterior region of the strap ends 34, 35, 87 and 88 are stitched with VELCRO-hook material 38, 40, 89 and 90 which is mateable with the VELCRO-loop material of the exterior region of the upper and lower portion 22 and 24 and flaps 70 and 72 of sleeve 12. The straps 14 and 16 have apertures 46 and 48. The apertures 46 and 48 are situated to provide a cupping action about the kneecap as the knee is bent and the kneecap protrudes.

The soft, non-rigid hooks 18 and 20 are made of nylon webbing or other soft material which totally eliminates the use of any hardware or rigid material in the brace which would reduce risk of injury in case of a fall or impact and upon which tension can be applied. The soft, non-rigid hooks 18 and 20 are separately anchored at ends 50 and 52 with stitching onto the exterior region of flaps 70 and 72 of sleeve 12. The soft, non-rigid hooks 18 and 20 are situated to rest almost directly behind the knee with soft, non-rigid hook 18 being anchored above the knee or on the thigh-side of the knee and soft, non-rigid hook 20 being anchored below the knee or on the calf-side of the knee. Strap portions 85 and 86 are always already pulled through the soft, non-rigid hooks 18 and 20 permitting the user to apply the desired tension to the strap portions 85 and 86 of straps 14 and 16 by pulling the strap ends 34 and 36, then looping strap ends 34 and 36 over soft, non-rigid hooks 18 and 20 and back towards the opposite side of the knee, where the VELCRO-hook material 40 of strap 36 mates with the VELCRO-loop material 62 of sleeve 12.

With references to FIGS. 2, 4 and 7, the knee brace 10 is shown with the straps 14 and 16 being extended in criss-cross fashion over the kneecap region. The straps 14 and 16 are looped about the soft, non-rigid hooks 18 and 20, respectively. Soft, non-rigid hook 20 snares strap 14, preventing strap 14 from slipping towards the thigh-side of the kneecap as strap 14 is drawn tight. Finally, strap 14 is looped back over soft, non-rigid hook 20 and onto the lower portion 24 of sleeve 12 where the VELCRO-hook material 38 of the strap end 34 mates with the VELCRO-loop material 62 of the sleeve 12. Similarly, soft, non-rigid hook 18 snares strap 16, preventing strap 16 from slipping towards the calf-side of the kneecap as strap 16 is drawn tight. Strap 16 is looped back over soft, non-rigid hook 18 and onto the upper portion 22 of sleeve 12 where the VELCRO-hook material 40 of the strap end 36 mates with the VELCRO-loop material 62 of the sleeve 12.

Accordingly, each of the straps 14 and 16 may be drawn to the desired tension level by the user by separately drawing strap portion 85 of strap 14 and strap portion 86 of strap 16, and fastening the strap ends 34 and 36 to the front of the lower and upper portions 22 and 24 of the sleeve 12. The strap portions 81 and 82 of straps 14 and 16 are designed to be drawn from the front and center of the kneecap opening 13 around the sides of the knee and fastening strap-ends 87 and 88 behind the knee mating with VELCRO-loop material on flaps 70 and 72 of sleeve 12. The user is able to add tension to the strap portions 81 and 82, accordingly, by fastening strap ends 87 and 88 further along behind the knee on flaps 70 and 72 of sleeve 12.

It is therefore to be understood that the following claims are intended to cover all of the generic and specific features of the present invention herein described, and all statements of the scope of the invention which as a matter of language, might be said to fall between. It is further being understood by those skilled in the art that the foregoing description is in terms of preferred embodiments of the present invention wherein various changes and modifications may be made without departing from the spirit and scope of the invention, as set forth in the appended claims.

Now that the invention has been described,

What is claimed is:

1. A knee brace or wrap for use during athletic or other activity to prevent or reduce knee damage, said knee brace comprising:

sleeve means for snugly embracing the knee joint region of a user's leg and adjacent sections of the upper limb and lower limb extending therefrom, said sleeve means containing an opening positionable directly over the front of the kneecap;

first and second strap means, said strap means criss-crossing one another and intersecting directly over the front of the kneecap; each strap means having an aperture positionable directly over the front of the kneecap for providing tension that encompasses the kneecap; said strap means each being anchored above and below said sleeve means opening to said sleeve means at points above and below the aperture of each strap respectively; and adjustment means for adjusting the tension of said first and second strap means across the kneecap and sides of the knee and to the back of the knee.

2. A knee brace as set forth in claim 1, said sleeve means further comprising first and second side portions adjacent respective sides of the kneecap and extending longitudinally along the user's leg;

said first and second strap means each further comprising a first and second strap end;

said first strap end of said first strap means being adjustably anchored by said adjustment means to said first side portion of said sleeve means adjacent a section of the upper limb;

said first strap end of said second strap means being adjustably anchored by said adjustment means to said first side portion of said sleeve means adjacent a section of the lower limb;

said second strap end of said first strap means being adjustably anchored by said adjustment means to said second side portion of said sleeve means adjacent a section of the upper limb;

and said second strap end of said second strap means being adjustably anchored by said adjustment means to said second side portion of said sleeve means adjacent a section of the lower limb.

3. A knee brace a set forth in claim 1, said sleeve means comprising:
an elongate length wrap-able about the knee joint and knee region of a user; and,
adjustable fastenable means positioned behind the knee for adjusting tension of said sleeve means and securing said elongate length about the knee region of a user.

4. A knee brace as set forth in claim 1, said adjustment means comprising:
tensioning means for tensioning said strap means to criss-cross with intersection directly across the kneecap, said tensioning means being anchored to said sleeve means; and,
fastening means for fastening said strap means under tension to said sleeve means.

5. A knee brace as set forth in claim 3, said sleeve means including
an inner portion
an outer portion
a first end and
a second end;
said second end overlaying said first end,
said inner portion at said second end including a first hook and loop material portion,
said outer portion at said first end including a second hook and loop material portion,
said adjustable fastening means comprising said first and second hook and loop material portion,
said material portion being mateable with second hook and loop material portion behind the knee joint and creating an opening behind the knee joint located between mateable portions.

6. A knee brace as set forth in claim 4, said tensioning means comprising
a first and second soft, non-rigid hook anchored to said second side portion of said sleeve means adjacent the upper limb and lower limb, respectively,
said first strap being loopable about said second soft, non-rigid hook, and,
said second strap being loopable about said first soft, non-rigid hook.

7. A knee brace as set forth in claim 4, each of said first and second strap ends of said first and second strap including a first portion of hook and loop material
said sleeve means being made of hook and loop material oriented for mateable engagement with said first and second strap ends.

8. A knee brace as set forth in claim 5, said soft, non-rigid hooks comprising of soft, non-rigid material designed to reverse direction of tension on said first and second straps.

* * * * *